(12) United States Patent
Müller-Bruhn et al.

(10) Patent No.: US 12,741,154 B2
(45) Date of Patent: Sep. 22, 2026

(54) RESPIRATION PROMOTING APPARATUS AND USE THEREOF

(71) Applicant: STIMIT AG, Biel/Bienne (CH)

(72) Inventors: Ronja Müller-Bruhn, Windisch (CH); Thomas Degen, Birmensdorf (CH)

(73) Assignee: STIMIT AG, Biel/Bienne (CH)

( * ) Notice: Subject to any disclaimer, the term of this patent is extended or adjusted under 35 U.S.C. 154(b) by 948 days.

(21) Appl. No.: 17/999,142

(22) PCT Filed: May 18, 2021

(86) PCT No.: PCT/EP2021/063212
§ 371 (c)(1),
(2) Date: Nov. 17, 2022

(87) PCT Pub. No.: WO2021/239523
PCT Pub. Date: Dec. 2, 2021

(65) Prior Publication Data

US 2023/0218917 A1 Jul. 13, 2023

(30) Foreign Application Priority Data

May 18, 2020 (CH) .................................... 00603/20

(51) Int. Cl.
*A61N 2/02* (2006.01)
*A61N 2/00* (2006.01)

(52) U.S. Cl.
CPC ............... *A61N 2/006* (2013.01); *A61N 2/02* (2013.01)

(58) Field of Classification Search
CPC .................................................. A61N 2/00–12
See application file for complete search history.

(56) References Cited

U.S. PATENT DOCUMENTS

| | | | |
|---|---|---|---|
| 10,485,977 B1 | 11/2019 | Feinstein | |
| 2012/0016280 A1 | 1/2012 | Aliverti et al. | |
| 2015/0142082 A1 | 5/2015 | Simon et al. | |
| 2016/0310730 A1 | 10/2016 | Martins et al. | |
| 2019/0001127 A1 | 1/2019 | Evans et al. | |
| 2019/0117975 A1 | 4/2019 | Grossman et al. | |
| 2019/0262616 A1 | 8/2019 | Carroll | |
| 2020/0368523 A1* | 11/2020 | Fuller | A61N 1/0551 |

FOREIGN PATENT DOCUMENTS

| | | |
|---|---|---|
| CN | 109908476 A | 6/2019 |
| JP | 2001029485 A | 2/2001 |
| NZ | 614757 A | 8/2015 |
| WO | 2019154839 A1 | 8/2019 |
| WO | 2021074453 A1 | 4/2021 |

OTHER PUBLICATIONS

International Search Report and Written Opinion issued Oct. 6, 2021 in Intl. Appl. No. PCT/EP2021/063212.

* cited by examiner

*Primary Examiner* — Thaddeus B Cox
(74) *Attorney, Agent, or Firm* — MEDLER FERRO WOODHOUSE & MILLS PLLC

(57) ABSTRACT

A respiration promoting apparatus and a method for promoting respiration for coordinately stimulating a phrenic nerve of a patient for activating a diaphragm of the patient by a pulsating field that is produced by interference stimulation principles.

23 Claims, 7 Drawing Sheets

RESPIRATION PROMOTING APPARATUS AND USE THEREOF

TECHNICAL FIELD

The present invention relates to an electric respiration promoting apparatus for stimulating a phrenic nerve of a human or animal being and a use of the respiration promoting apparatus in a method for promoting respiration of a human or animal. More particularly, the present invention relates to a non-invasive electro-magnetic respiration promoting apparatus using a treatment envelope produced by interference stimulation at the phrenic nerve.

BACKGROUND ART

In medicine, it is known that for many purposes it is beneficial to activate a target tissue of a patient using stimulation by electric or magnetic fields. For achieving such activation of tissues in a patient's body, it is known to directly stimulate the tissue or to indirectly activate the tissue via stimulation of specific parts of the neural system. For example, the target tissue being a muscular tissue can be activated by providing electric pulses directly to the muscular tissue or to nerves associated to the muscular tissue.

Practicing the 1989s and 1990s, electric stimulators consisting of an electrode pair were used to simulate a phrenic nerve, however this method is painful for patients. The method was replaced by electro-magnetic stimulation of the phrenic nerves, which was thereafter considered the "gold standard" for phrenic nerve stimulation because the magnetic fields penetrate deeper into the tissue and it's use for phrenic nerve stimulation produces no pain or only minor discomfort if used with newer generation coil designs. Both methods are usually applied at the neck region, where the phrenic nerve is closest to the skin surface and therefore easier to stimulate with these methods. However, the limitation of using both standard electric stimulation with an electrode pair and electro-magnetic fields for the phrenic nerve application is, that superficial tissue including neck muscles are always co-stimulated, which may result in discomfort if used over a long time. Also heating occurs if coils are used to produce electro-magnetic fields. Especially magnetic stimulation cannot target one particular area inside the body, and therefore always other surrounding non-target areas are co-stimulated.

In critical care units of hospitals, it may be desired to activate the diaphragm of ventilated patients in order to prevent drawbacks of disuse of the diaphragm. It was shown that disuse atrophy of diaphragm muscle fibres occurs already in the first 18-69 hours of mechanical ventilation, and the muscle fibre cross-sections decreased by more than 50% in this time. Thus, it is aimed to activate the diaphragm repeatedly while the patient is given artificial or mechanical respiration such that the functioning of the diaphragm can be upheld, or to activate the diaphragm at least during the weaning period to support effective restoration of independent respiratory function.

It is known that the diaphragm can be activated by stimulating at least one of the two Phrenic nerves, e.g., at the neck of the patient. In this context, U.S. 2016/0310730 A1 describes an apparatus for reducing ventilation induced diaphragm disuse in a patient receiving ventilation support from a mechanical ventilator. The apparatus includes an electrode array of first and second types and comprises a plurality of electrodes configured to stimulate a Phrenic nerve of the patient, and at least one controller identifying a type of electrode array from at least two different types, and generating a stimulus signal for stimulating a Phrenic nerve of the patient based upon the identity of the electrode type. Such electrode pair-based stimulation is reported to be painful. Furthermore, it is not very robust to patient movements or relocations, and the possible stimulation depth can be significantly limited by bones or fatty tissue and painful sensations.

There are a number of patent applications for general interference stimulation in use, e.g., to treat cardiac issues U.S. Pat. No. 10,485,977B1, for spinal cord stimulation U.S. 2019262616A1, treatment of lower pelvic, sacral, lumbar and abdominal regions NZ614757A, and some other applications. In conventional interference stimulation, four stimulating electrodes are positioned in a crisscross pattern, in which each electrode is located at a corner of a rectangle, typically a square. Thus, the line segment that joins the electrodes of one electrode pair is one diagonal of the rectangle, and the line segment that joins the electrodes of the other electrode pair is the other diagonal of the rectangle. These two diagonals cross each other, forming an X (crisscross) pattern. These electrodes are positioned so that the target tissue region is located at, or beneath, the center of the rectangle where the two criss-crossing diagonals intersect. However, a rectangular configuration of stimulating electrodes may sometimes be difficult to realize at the neck region. The criss-crossed electrodes produce multiple, separate regions where the treatment envelope occurs.

To stimulate one target area in the deep brain using interference stimulation specifically, U.S. 2019/0117975 A1 describes a special method and apparatus to stimulate one specific target area. It is described as a drawback that the crisscrossed electrodes produce multiple separate regions where the maximum envelope amplitude occurs, and an electrode configuration to make sure that only one maximum envelope amplitude occurs is described.

Therefore, there is a need for a non-invasive respiration promoting apparatus and use thereof and a non-invasive method for promoting respiration of a patient, which allow for efficient stimulation of both Phrenic nerves, overcome space constrains, avoid co-stimulation effects of tissue in the vicinity of the Phrenic nerves, are simple to apply at a patient as well as are convenient and pain-free for the patient.

SUMMARY OF INVENTION

According to the invention this need is settled by a respiration promoting apparatus and a method for promoting respiration defined by the features of independent claims. Preferred embodiments are subject of the dependent claims.

In one aspect, the present invention provides a respiration promoting apparatus for co-ordinately stimulating a phrenic nerve of a human, comprising: a first field generator configured to generate a first spatial field having a first frequency and a first amplitude, and a second field generator configured to generate a second spatial field having a second frequency and a second amplitude. The apparatus further comprises a control unit configured to control the first and the second frequencies so that the first and second spatial fields constructively and destructively interfere with each other, thereby forming a pulsating field for stimulating the phrenic nerve. The control unit is further configured to adjust the pulsating field so that the phrenic nerve is positioned in the pulsating field.

In another aspect, the present invention provides a method for promoting respiration by stimulating a phrenic nerve of a human, wherein the method comprises the steps of generating a first spatial field and a second spatial field having a first frequency and a second frequency and a first amplitude, and generating a second first spatial field having a second frequency and a second amplitude. The method further comprises the steps of controlling the first and the second frequencies so that the first and second spatial fields constructively and destructively interfere with each other, thereby forming a pulsating field for stimulating the phrenic nerve; and adjusting the pulsating field so that the phrenic nerve is positioned in the pulsating field.

The term “spatial field” as in context of the aspects of the invention described below relates to any field allowing stimulation of a target tissue of a patient. It may particularly involve an electric field or a magnetic field or an electro-magnetic field. Such fields allow for directly stimulate muscular structures or indirectly stimulate muscular structures via the nervous system or via other muscular structures.

The term “field generator” relates to an electric circuit including either two electrodes or a coil for generating a spatial field, i.e., an electric field or a magnetic field, respectively, or an electro-magnetic field.

Preferably, the first and the second frequencies are adjacent or neighbouring to each other in a frequency spectrum. The term “adjacent” or “neighbouring” in connection with the frequencies of the spatial fields means that the frequencies have similar but not the same value, i.e. the frequencies are slightly different. In other words, the first frequency deviates from the second frequency slightly, e.g., in a range of 0.1%, 0.2%, 0.5%, 1%. For example, the first frequency is 4995 Hz, while the second frequency is 5005 Hz so that the two fields can interfere with each other.

The term “pulsating field” relates to a spatial field that is formed by overlapping, more specifically, by an interference between the first and the second spatial fields. In other words, the first and the second spatial fields interfere with each other and result in the pulsating field that can be used for stimulating the phrenic nerve.

The term “threshold amplitude” for a given excitable cell means the minimum amplitude of a single electric field pulse that evokes an action potential in a given cell.

The term “sub-threshold amplitude” for a given excitable cell means an amplitude that is less than the threshold amplitude for a given cell.

The term “interfere” in connection with two spatial fields is a phenomenon in which the two waves of the two spatial fields superpose to form a resultant wave, which is greater, lower or the same amplitude. Constructive and destructive interference result from the interaction of waves that are correlated or coherent with each other. The term “superpose” refers to overlap of fields according to the superposition principle.

The term “treatment envelope” refers to an area of the spatial field at which the amplitude of the amplitude-modulated waveform is higher than the threshold amplitude of the target nerve. In this area, multiple sub-threshold peaks in temporal succession can evoke an action potential in the target nerve. The pulsating field can be represented in a frequency domain as a treatment envelope which is positioned at the phrenic nerve. The pulsating field, or in other words the treatment envelope, can stimulate the phrenic nerve of a patient, thereby activating a diaphragm of the patient.

The term “beat” in connection with interference refers to an interference pattern between two electro-magnetic fields with slightly different frequencies, perceived as a periodic variation in fields strength whose rate is the difference of the two frequencies.

In an exemplary embodiment, the invention may comprise a first electrical network creating a first electric field between electrodes in a first pair of electrodes and a second electrical network creating a second electric field between electrodes in a second pair of electrodes, such that the first and second electric fields constructively and destructively interfere with each other to create an amplitude-modulated waveform and the largest envelope amplitude of the amplitude-modulated waveform occurs in the target area or in the treatment envelope or at a phrenic nerve. Different electrode configurations are possible to excite two phrenic nerves co-ordinately: side-by-side or criss-cross. The spatial position of at least two treatment envelopes shall overlap with the phrenic nerve locations.

The apparatus may drive at least two isolated currents in order to cause at least two stable action potential oscillations of neurons. These stable action potential oscillations are achieved by a train of electric field pulses with a sub-threshold amplitude and a frequency higher than the neurons' natural band such that the inter-pulse interval is sufficiently small to achieve supra-threshold temporal summation. The two currents interfere with each other to produce an amplitude-modulated, AM, waveform. The AM waveform has a frequency, sometimes called the beat frequency, in the neurons' natural band and has a supra-threshold amplitude. The AM waveform allows sufficient repolarization between action potentials. The AM waveform evokes a stable train of time-locked action potentials in the neurons. When two alternating waves of different frequencies overlap, they create an alternating wave with an effective frequency that is equal to the average of the two original frequencies and an amplitude that changes periodically at a frequency that is equal to the difference of the original frequencies. The amplitude modulation is due to a periodic change between a constructive interference, e.g., when the two waves are nearly in phase, and a destructive interference, when the two waves are nearly 180 degrees out of phase. The frequency in which the amplitude changes is sometimes called a beat frequency, an amplitude modulation frequency, or an envelope frequency. The average of the two original frequencies is often called the carrier frequency.

By spatially overlapping two fields, the amplitude of superimposed fields is modulated at a rate equal to the difference between the fields frequencies and at a maximal strength equal to the sum of the field amplitudes. This principle is called “interferential summation” and the resulting AM frequency is sometimes called “beat frequency”. The location and spread of the AM field depend in part on the positioning of the stimulation electrodes relative to each other. In an exemplary embodiment, the apparatus drives two currents, such as a first alternating current produced by a first pair of electrodes and a second alternating current produced by a second pair of electrodes, through a conducive biological medium.

In some implementation of this invention, electric fields are applied via electrodes. In some other implementations, an electric field is generated from an inductive source, e.g. coil, using a time-varying magnetic field. In some cases, the current sources produce an electric field pulse. The pulse may have different shapes, e.g. rectangular, sine, etc. In use scenarios that evoke an electric field pulse train, the train may be of any polarity, symmetrical or asymmetrical, or sinusoidal.

In an exemplary embodiment, the control unit is configured to adjust the first amplitude of the first spatial field and/or the second amplitude of the second spatial field, preferably as well as a distance between the first and the second spatial fields, such that the phrenic nerve is positioned within the pulsating field. In other words, the treatment envelope is positioned at the phrenic nerve.

Further, the control unit may also be configured to adjust the first frequency of the first spatial field and the second frequency of the second spatial fields to modify the frequency of the pulsating field.

By adjusting the amplitudes, the location of the maximal amplitude can be defined, thereby varying the position or physical location of the pulsating field. This is because the amplitude of the fields decay with distance from the source. If one amplitude is larger the maximal amplitude is closer to that source.

Preferably, the adjustment of the pulsating field, in particular by adjustment of the first amplitude of the first spatial field and the second amplitude of the second spatial field, may be based on spatial location information of the treatment envelope, i.e., the amplitude of the pulsating field, where an amplitude of the amplitude-modulated waveform is greatest.

Preferably, at least one of the first and second field generators is anti-phasic. In other words, the first and second field generators are not in phase.

Preferably, the pulsating field has a first amplitude-modulated waveform with an interference pattern.

Preferably, the first and second spatial fields are superposed and the interference pattern that is a beat.

Preferably, an amplitude of the first amplitude-modulated waveform exceeds a predefined threshold which defined the minimum value of the amplitude that is sufficient for stimulating the phrenic nerve.

Preferably, the apparatus further comprises a third field generator configured to generate a third spatial field, and a fourth field generator configured to generate a fourth spatial field, wherein the third and fourth spatial fields constructively and destructively interfere with each other to generate a further pulsating field so that a further phrenic nerve is positioned in the further pulsating field.

The phrenic nerve and the further phrenic nerve may be referred to as the left and the right phrenic nerve. In other words, the respiration promoting apparatus enables the generation of a localized treatment envelope which may be applied for targeted stimulation of the phrenic nerves.

Preferably, an amplitude the pulsating field exceeds the predefined threshold that can stimulate the phrenic nerve. Further, an amplitude the further pulsating field exceeds the predefined threshold that can stimulate the further phrenic nerve Preferably, each of the field generators comprising a pair of electrodes having two electrode patches, each of which includes of a body attachment structure and a multiplicity of electrodes that are mechanically attached to the body attachment structure.

Preferably, the apparatus comprises a biofeedback sensor configured to be positioned at the patient such that it provides a feedback signal when a contraction of a diaphragm of the human occurs.

Such biofeedback sensors can efficiently detect activation of the diaphragm such that the electric field can be calibrated, and proper functioning of the stimulation can be monitored.

Preferably, the control unit is operably coupled to the biofeedback sensor and configured to adjust the pulsating field until the feedback signal is received. That is as soon as the contraction of a diagram occurs, the biofeedback sensor determines the contraction and issues the feedback signal. The feedback signal has a strength and a form that can be unambiguously determined or identified by the control unit. It means, the pulsating field is capable to simulate the phrenic nerve that causes the contraction, and hence, no further adjustment is required. In other words, the adjustment of the pulsating field can be made as soon as the patient begins to breath.

Preferably, the control unit is operably coupled to the biofeedback sensor and configured to automatically adjust the pulsating field until the feedback signal is received.

Preferably, the control unit being configured and arranged to automatically localize the first and/or second phrenic nerve with respect to the field generators that is effective, when appropriately energized, for stimulating the first and/or second phrenic nerve to produce a diaphragm contraction.

Preferably, the control unit is further configured and arranged to repetitively outputting stimulation signals by the field generators when such a determination is made by the control unit.

Preferably, the time of stimulation of the phrenic nerve differs from the time of stimulation of the further phrenic nerve, in order to distinguish the response of the biofeedback sensor.

Preferably, wherein a distinct timely expectation window of the feedback signal of the biofeedback sensor as a response to the stimulation of the first phrenic nerve supports spatial positioning of the amplitude of the first treatment envelope at the first phrenic nerve, and wherein a distinct timely expectation window of the feedback signal of the biofeedback sensor as a response to the stimulation of the second phrenic nerve supports spatial positioning of the amplitude of the second treatment envelope at the second phrenic nerve.

Preferably, the respiration promoting apparatus further comprises a second biofeedback sensor coupled to the control unit.

Preferably, wherein the first biofeedback sensor is associated to the first and second spatial fields and the second biofeedback sensor is associated to the third and fourth spatial fields.

Preferably, the first and second pairs of electrodes are positioned on the neck of a person in such way that the first pair of electrodes is positioned entirely on one side of a geometric plan, wherein the second pair of electrodes is positioned entirely on another side of the geometric plane, and wherein the geometric plane intersects the neck of the person.

Preferably, a distance between a first pair of electrodes of the first spatial field is different than the distance of a second pair of electrodes of the second spatial field.

The method according to the present invention may further comprise the step of superposing the first and second spatial fields so that the interference pattern is a beat.

Preferably, the method further comprises the step of generating a third and a fourth spatial field, so that the third and fourth electric fields constructively and destructively interfere with each other to form a further pulsating field for stimulating a further phrenic nerve.

Preferably, the method comprises the step of controlling size, shaping, and positioning of the region by adjusting the amplitude and by adjusting placement of the first and second field generators.

Preferably, the method comprises the steps of positioning a biofeedback sensor at the human; and providing a feedback signal using the biofeedback sensor when a contraction of a diaphragm of the human occurs.

Preferably, the method comprises the steps of adjusting the pulsating field until the feedback signal is received.

Preferably, the method comprises the steps of operably coupling a control unit to the biofeedback sensor, and automatically adjusting the pulsating field until by the control unit the feedback signal is received.

Preferably, the method comprises the steps of coupling a control unit operably to the biofeedback sensor, automatically localizing, by the control unit, the phrenic nerve with respect to a given set of electrodes, and repetitively outputting stimulation signals by the first and the second generators upon receiving the feedback signal.

Preferably, the method comprises the steps of supporting spatial positioning of the pulsating field at the first phrenic nerve by a distinct timely expectation window of the feedback signal of the biofeedback sensor as a response to the stimulation of the phrenic nerve, and supporting spatial positioning of the further pulsating field at the further phrenic nerve by a distinct timely expectation window of the feedback signal of the biofeedback sensor as a response to the stimulation of the further phrenic nerve.

Preferably, the first and the second spatial field are generated by a first and second electrode pair respectively, wherein each of first and second electrode pair comprises two electrode patches, and wherein each of the electrode patches includes of a body attachment structure and a multiplicity of electrodes that are mechanically attached to the body attachment structure as to be in a predetermined orientation.

Preferably, the method comprises the steps of positioning the first generator on the neck of the human that is entirely on one side of a geometric plan; and positioning the second field generator on the neck of the human that is entirely on another side of the geometric plane, and wherein the geometric plane intersects the neck of the person.

Preferably, the steps of controlling size, shaping, and positioning of the pulsating field are performed by adjusting relative amplitudes of the first and the second spatial fields and by adjusting placement of the first and the second field generator.

Preferably, an electric field can be generated by an inductive source such as coil using time-varying magnetic fields.

Preferably, the step of adjusting the pulsating field includes the step of adjusting the first and/or the second frequency to vary the frequency of the pulsating field.

The control unit may comprise a spatial field adjustment mechanism that is configured to automatically adjust or vary a field strength or an amplitude of the spatial field. Particularly, when a desired feedback from the biosensors is reached, the field can be reduced and adjusted. Thus, the control unit allows to efficiently adjust and dimension of the electric field or its required shape in order to achieve optimal (maximal) effect on the phrenic nerves or diaphragm with minimum energy applied and/or minimum effect on surrounding tissue. Preferably, each electric field creator consists of a plurality of electrodes (electrode array) on which each electrode can be activated or deactivated automatically to not only vary and optimize position of the source of the electric fields to produce optimal (maximal effect on the phrenic nerves/diaphragm with minimum energy applied and/or minimum effect on surrounding tissue, but also to automate this process without manual handling needs by the user. In case of patient movement and loss of function, such system can automatically vary electrode configurations to relocate the target area.

Such an apparatus allows for efficient stimulation of both Phrenic nerves by generating and optimizing the shape of the electric field characteristics provided by the first and the second coil units. Further, the apparatus overcomes space constrains by providing flexible positioning of the coil units generating the stimulating electric fields. The resulting electric field characteristics can avoid co-stimulation effects on tissue surrounding the Phrenic nerves. Also, the apparatus is simple to apply around a patient's neck and it is convenient and pain-free for the patient.

The use of electrical interference to stimulate a phrenic nerve is particularly advantageous, because only the targeted nerve will be stimulated, and no other tissue or superficial muscles will be co-activated. Compared to standard electric stimulation, no pain is expected. The requirements to use interferential stimulation for the application of phrenic nerves differ significantly from other previously described applications: two areas must be stimulated simultaneously (two phrenic nerves), the system must be especially robust to movements by the patient and electrodes need to be placed on soft, sometimes movable tissue, e.g., neck, instead of the rigid scull. The phrenic nerves shall be depolarized via so-called trains at a frequency of 10-35 Hz (inter-pulse frequency) over a period of 0.5-2 seconds to produce inhalation, with an intertrain break of 1-3 seconds to allow exhalation. Synchronization to patient's spontaneous breathing efforts is advantageous in case of spontaneous breath, as well as synchronization to a ventilator in case of additional ventilation.

Also, the use of interference stimulation for two targeted peripheral nerves in particular, or the use of interference stimulation to intentionally target two target areas inside the body is nowhere described.

Ideally, two treatment envelopes are produced that activate the two phrenic nerves. However, more flexibility may be required of the location of the two phrenic nerve varies from person to person. Moreover, more flexibility to adjust each treatment envelope individually may be required, and/or feedback mechanisms using biofeedback sensors, if the patient moves and the treatment envelope must be readjusted to match the new phrenic nerve location.

BRIEF DESCRIPTION OF THE DRAWINGS

The respiration promoting apparatus and the method for promoting respiration of a patient according to the invention are described in more detail herein below by way of exemplary embodiments and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
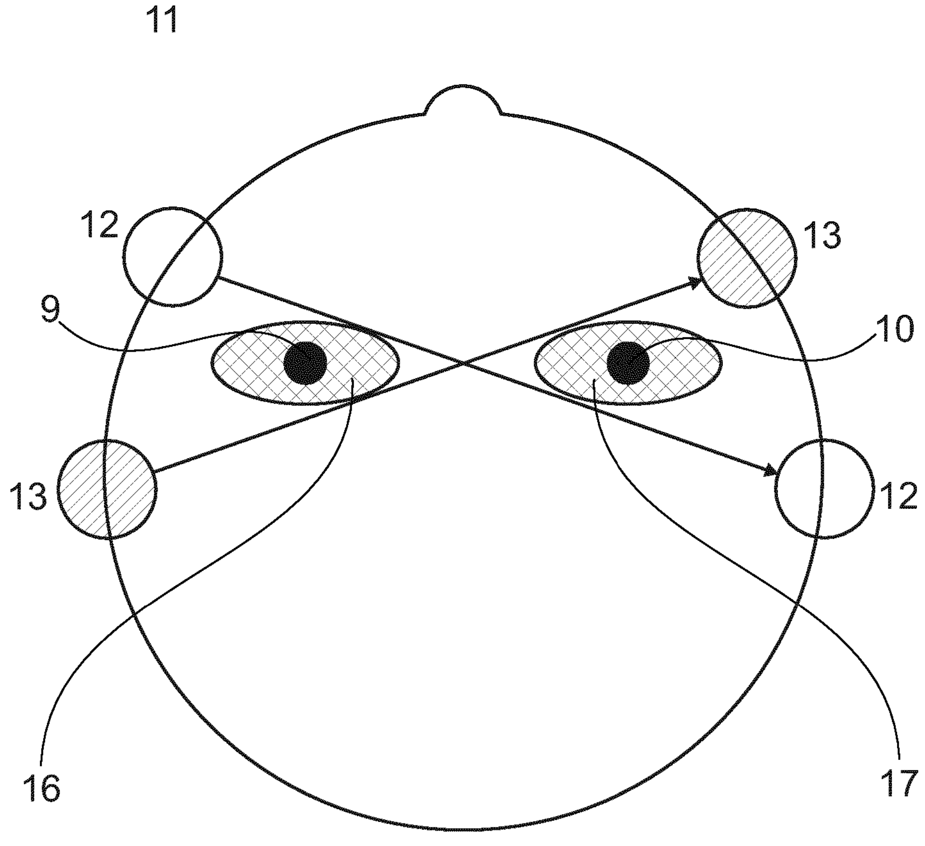
FIG. 1 shows a neck from the top view, and a conventional criss-cross configuration of two electrode pairs.

FIG. 1 shows a neck from the top view as indicated by reference sign 11, and a conventional criss-cross configuration of two electrode pairs 12, 13 that produce two pulsating fields 16, 17 respectively two treatment envelopes 16, 17. Thereby, the first respectively left phrenic nerve 9 lies in the first target area/treatment envelope 16 (first area of maximum amplitude) and the second respectively right phrenic nerve 10 lies in the second target area/treatment envelope 17 (second area of maximum amplitude).

Figure 2:
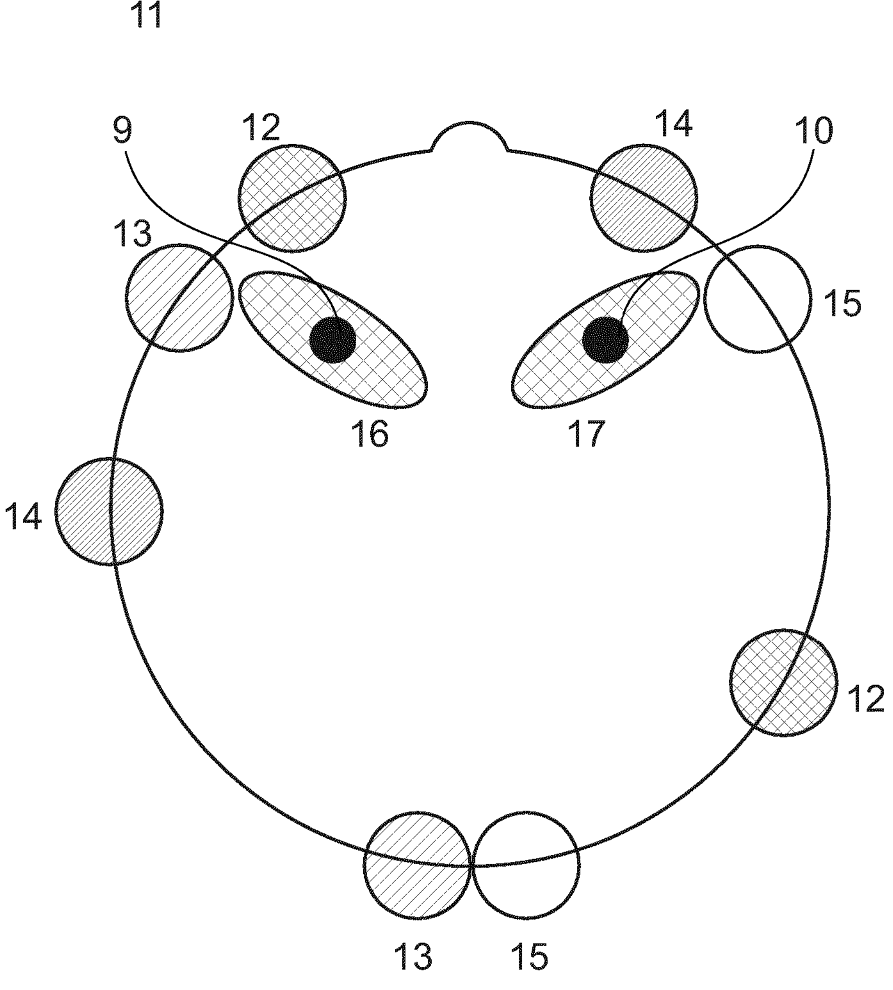
FIG. 2 shows a neck from the top vie, and a side-by-side configuration of electrode pairs comprising a total of four electrode pairs.

FIG. 2 shows a neck from the top view as indicated by reference sign 11, and a side-by-side configuration of electrode pairs comprising a total of four electrode pairs 12, 13, 14, 15, producing two pulsating fields with two treatment envelopes 16, 17. While this solution requires more electrode pairs, the location of the first pulsating fields with the treatment envelope 16 (left phrenic nerve 9) can be individually adjusted by replacing the relating two electrode pairs 12, 13 and the second pulsating fields with the second treatment envelope 17 (right phrenic nerve 10) can be individually adjusted by replacing the relating two electrode pairs 14, 15.

Figure 3:
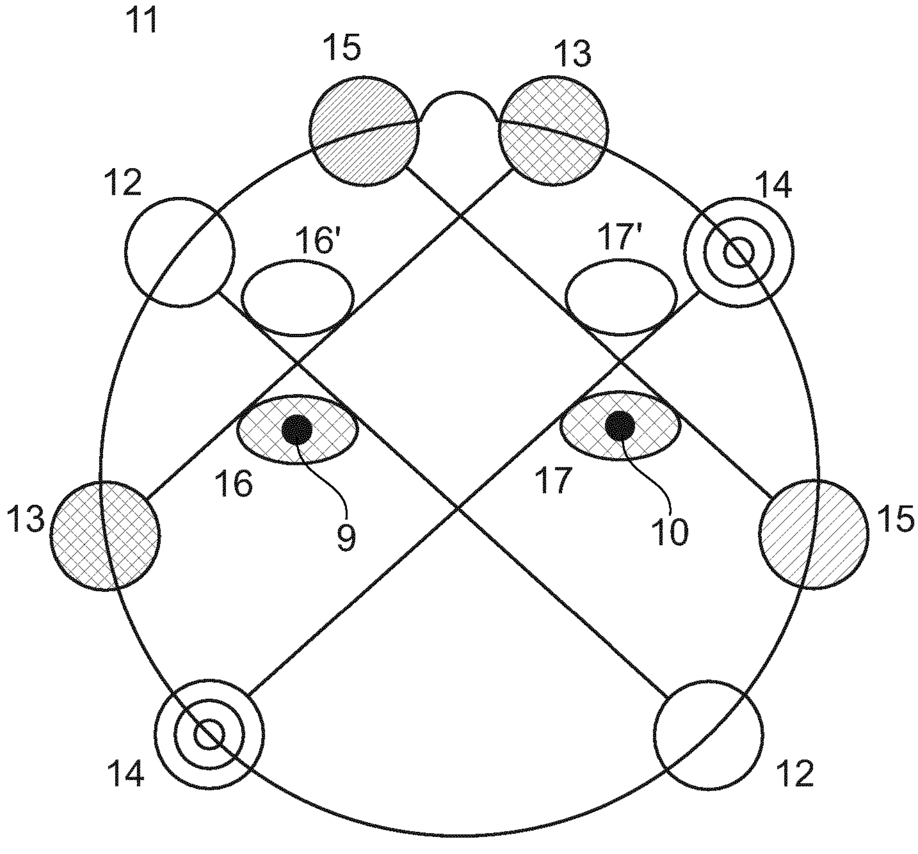
FIG. 3 shows a neck from the top view, and a conventional criss-cross configuration of four electrode pairs.

FIG. 3 shows a neck from the top view as indicated by reference sign 11, and a conventional criss-cross configuration of four electrode pairs 12, 13, 14, 15 that produce four treatment envelopes, wherein the left phrenic nerve 9 lies a first pulsating fields with the treatment envelope 16 and the right phrenic nerve 10 lies a second pulsating fields with the treatment envelope 17. The other two treatment envelopes 16', 17' remain unused in this case since none of the phrenic nerve is positioned therein.

Figure 4:
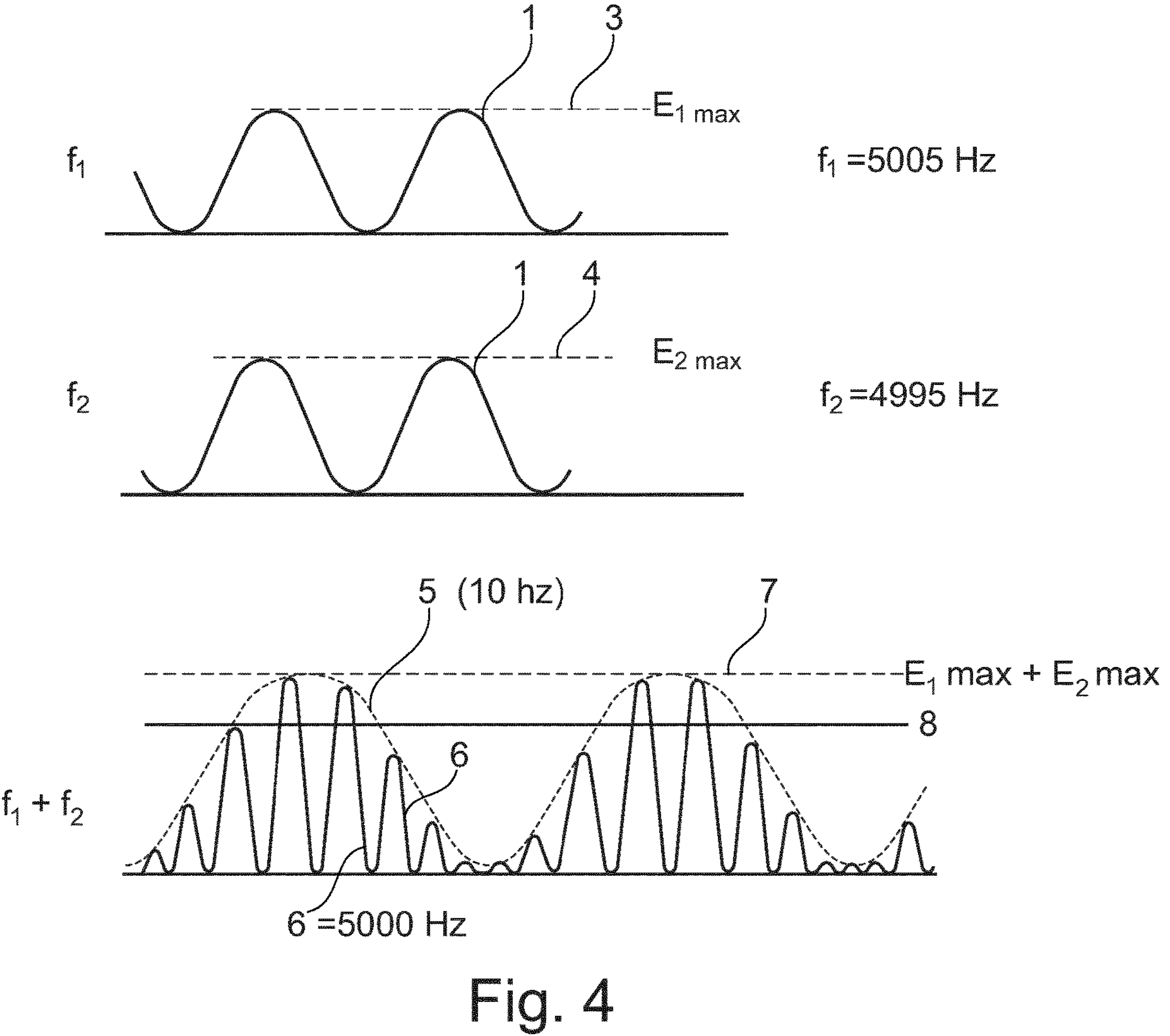
FIG. 4 shows a conceptual diagram that illustrates envelope amplitude with two current channels producing two original waveforms.

FIG. 4 is a conceptual diagram that illustrates envelope amplitude. Thereby, two current channels produce two original waveforms, wherein channel one produces original waveform 1 and channel two produces original waveform 2. The amplitude of original waveform 1 is E1 (3) and the amplitude of original waveform 2 is E2 (4). Interference of the two original waveforms 1, 2 produces an amplitude-modulated (AM) waveform 6. The top of the envelope is a signal 5. The peak amplitude of that signal is the envelope amplitude EN (7). Targeting is based on controlling the spatial position of a region where the envelope amplitude is above a threshold 8 (e.g. of the phrenic nerve) or is at a maximum, and this area is called treatment envelope.

Figure 5:
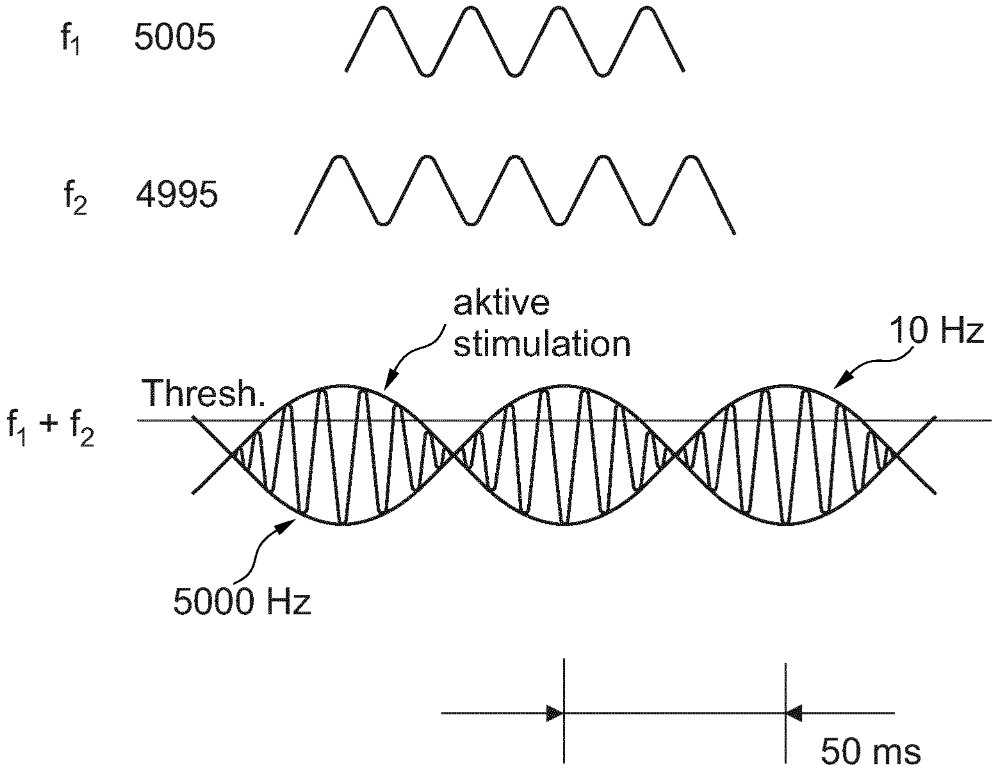
FIG. 5 shows an exemplary embodiment of an interference of the first and second spatial field in frequency domain, where the first spatial field has a first frequency $f_1$ and the spatial field has a second frequency $f_2$.
Figure 5:
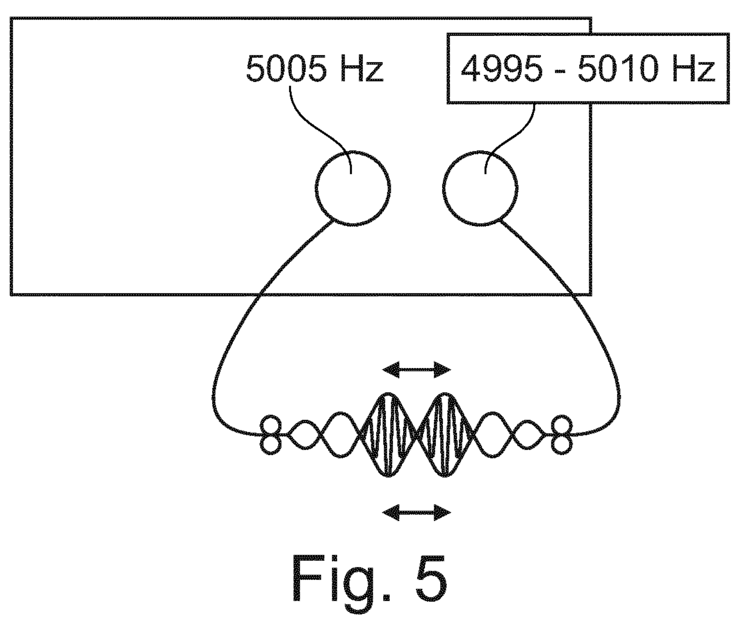

FIG. 5 shows an exemplary embodiment of an interference of the first and second spatial field in frequency domain, where the first spatial field has a first frequency $f_1$ and the spatial field has a second frequency $f_2$.

The two frequencies $f_1$ and $f_2$ are associated either to two pairs of electrodes and two electric fields respectively, or by two coils and two magnetic fields. The fields have similar but not identical frequency. For example, the first frequency is 4995 Hz while the second frequency is 5005 Hz. These two fields are preferably arranged so that they overlap or superpose with each other. The relevant point is between the two sources, assuming the fields have the same amplitude. The effect is the biggest in the middle between the two field sources, i.e., the fields from a point source decrease with a radius. The interference pattern of the two fields yields a beat with 10 Hz, i.e., $f_1$-$f_2$ and a carrier frequency of 5000 Hz which is $$\frac{(f_1 - f_2)}{2}.$$

Thus, the beat is located in the middle between the two field sources, the amplitude varies with 10 Hz, and the fundamental frequency of 5000 Hz is the active frequency. Considering the threshold, only a few wave crests can activate the nerves. There may be an activation pattern corresponding to the state of the art. The effective wave crests repeat at a frequency of 20 Hz, i.e., both maxima and minima of the 10 Hz envelope can lead to activation.

If the field generator is configured to coordinatedly emit both frequencies, it can be achieved, for example, that one frequency is fixed, e.g., 5005 Hz as described above, and the other can be adjusted, either by the user or by an intelligent algorithm that maximizes the feedback. If the second output is set to 4995 Hz, the interference pattern described above can obtained. By varying the second frequency slightly, the location of the maximum interference can be shifted back and forth between the two field generators, thereby control the point of maximum effect, where the basic frequency remains about 5000 Hz.

Figure 6:
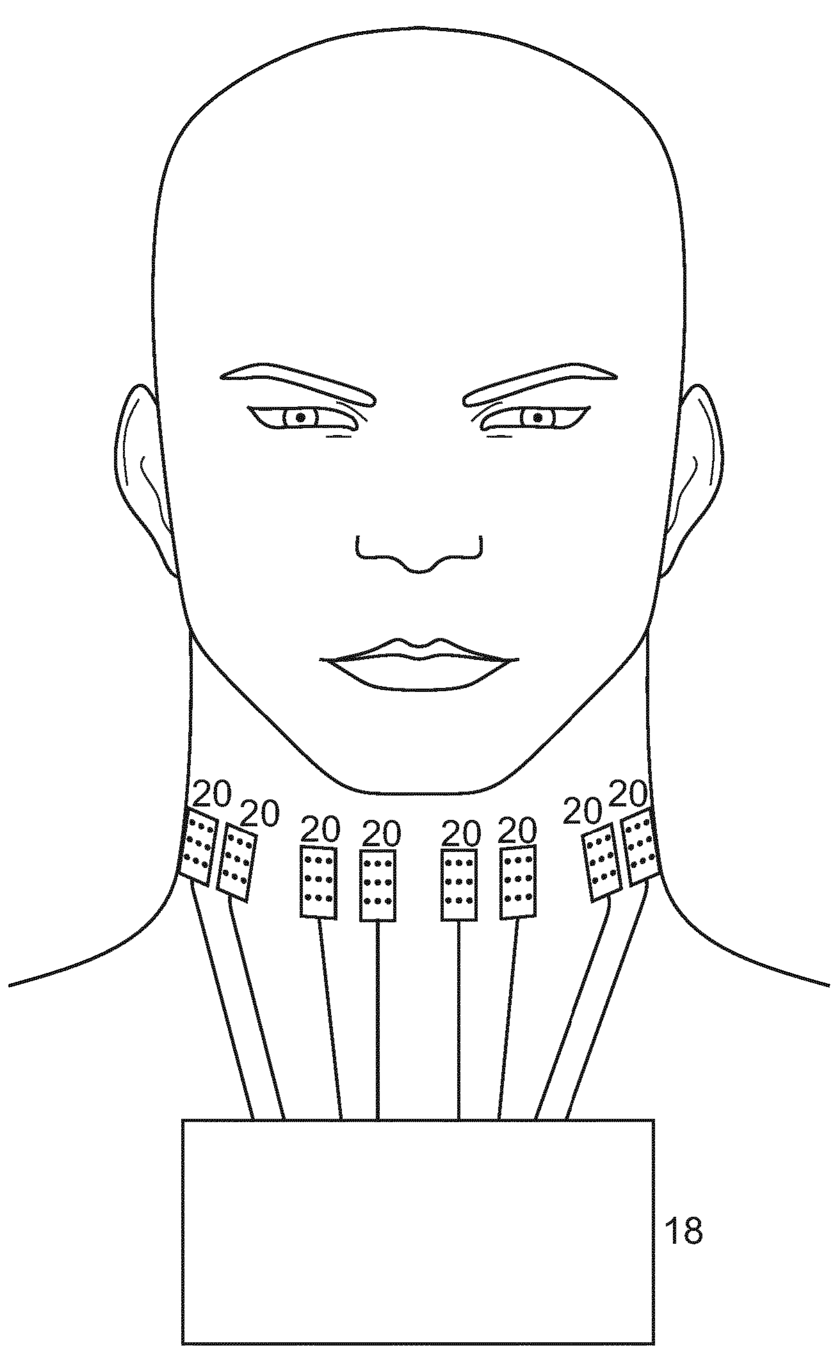
FIG. 6 shows a configuration with four electrode pairs of which each electrode position is selected from a multitude of electrodes.

FIG. 6 shows a schematic connectivity or arrangement of four electrode pairs, where each electrode position is selected from a multitude of electrodes comprised in an electrode array attached to an electrode patch 20. Each of these electrode patches 20 is connected to a control unit 18. In another embodiment of the present invention, the four electrode pairs can be replaced with four coils.

Figure 7:
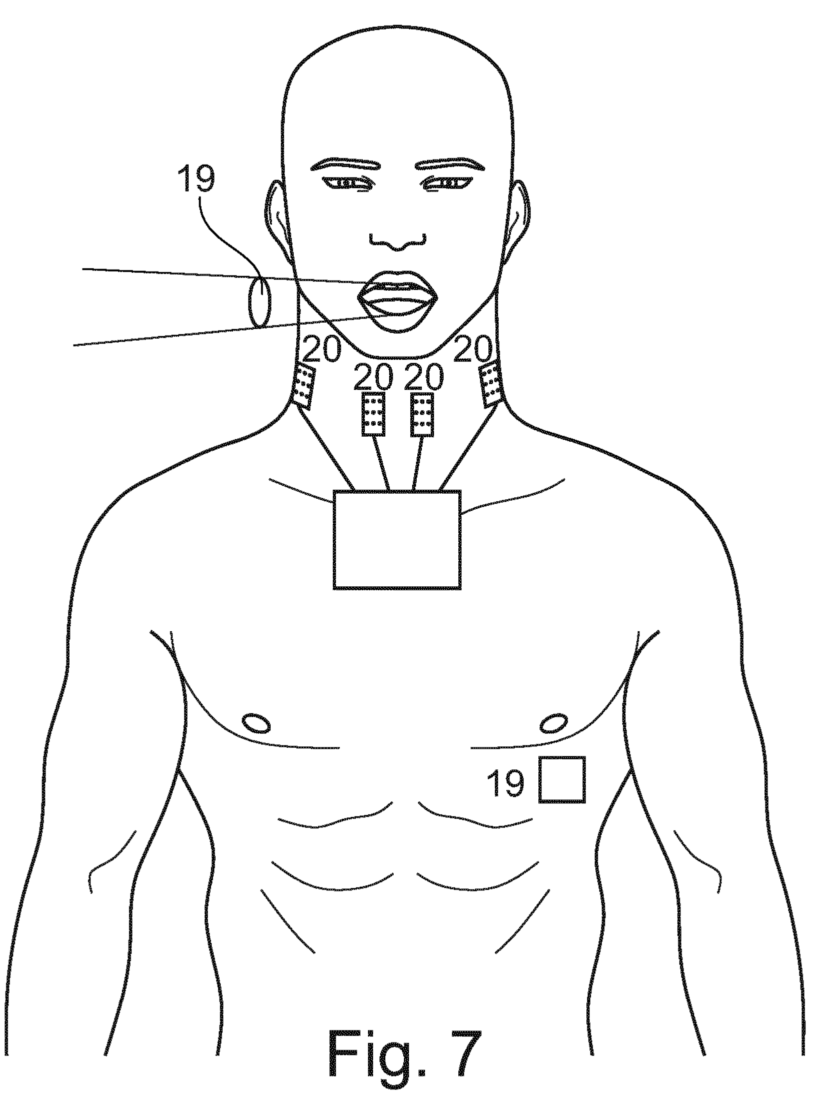
FIG. 7 shows a configuration with 2 electrode pairs of which each electrode position is selected from a multitude of electrodes comprised in an electrode array attached to an electrode patch (20), each of these connected to a controller, which is also connected to a biofeedback sensor (19)

FIG. 7 shows a schematic connectivity or arrangement of two electrode pairs, wherein each electrode position is selected from a multitude of electrodes comprised in an electrode array attached to an electrode patch 20. Each of these electrode patches 20 is connected to a controller 18; which is also connected to a biofeedback sensor 19 (e.g. pressure, flow, EMG or ultrasound etc.). Similar as above, in another embodiment of the present invention, the two electrode pairs can be replaced with two coils.

Figure 8:
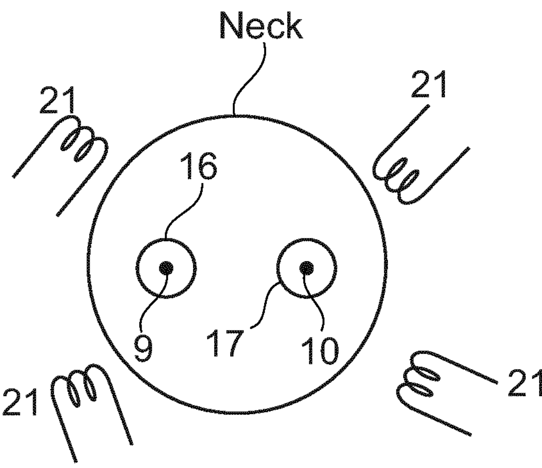
FIG. 8 shows a neck from the top view, and four electromagnetic coils placed around the neck.

FIG. 8 shows a neck from the top view as indicated by reference sign 11. In this embodiment, four electro-magnetic coils 21 are placed around the neck. The electro-magnetic coils 21 may or may not comprise a ferrite core, i.e. a magnetic core producing electro-magnetic fields with interference.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

LIST OF REFERENCE SIGNS

1 first waveform
2 second waveform
3 amplitude of first waveform
4 amplitude of second waveform
5 envelope of amplitude modulated waveform (=signal)
6 amplitude-modulated waveform
7 envelope amplitude ($E_N$)
8 threshold of (phrenic) nerve
9 left (first) phrenic nerve
10 right (second) phrenic nerve
11 top view neck
12 first electrode pair
13 second electrode pair
14 third electrode pair
15 fourth electrode pair
16 first target region=first treatment envelope
17 second target region=second area of maximum envelope amplitude=second treatment envelope
18 control unit
19 biofeedback sensor
20 electrode patch comprising electrode array
21 electro-magnetic coil with or without ferrite core

The invention claimed is:

1. A respiration promoting apparatus for co-ordinately stimulating a phrenic nerve of a human, comprising:
- a first field generator configured to generate a first spatial field having a first frequency and a first amplitude;
- a second field generator configured to generate a second spatial field having a second frequency and a second amplitude;
- a third field generator configured to generate a third spatial field;
- a fourth field generator configured to generate a fourth spatial field, and
- a controller configured to control the first frequency and the second frequency so that the first spatial field and the second spatial field constructively and destructively interfere with each other, thereby forming a pulsating field for stimulating the phrenic nerve,
- wherein the controller is further configured to adjust the pulsating field so that the phrenic nerve is positioned in the pulsating field,
- wherein the third spatial field and the fourth spatial field constructively and destructively interfere with each other to generate a further pulsating field so that a further phrenic nerve is positioned in the further pulsating field, and
- wherein the third spatial field and fourth spatial field constructively and destructively interfere with each other to generate a second amplitude-modulated waveform having a second interference pattern.

2. The respiration promoting apparatus of claim 1, wherein the controller is configured to adjust the first amplitude and/or the second amplitude of the first spatial field and the second spatial field such that the phrenic nerve is positioned within the pulsating field.

3. The respiration promoting apparatus of claim 1, wherein the controller is configured to adjust the first frequency and/or the second frequency of the first spatial field and the second spatial field.

4. The respiration promoting apparatus of claim 1, wherein the first frequency and the second frequency are adjacent to each other in a frequency spectrum such that the first frequency deviates from the second frequency in a range of up to 0.1%, 0.2%, 0.5%, or 1%.

5. The respiration promoting apparatus of claim 1, wherein at least one of the first field generator and the second field generator is not in phase.

6. The respiration promoting apparatus of claim 1, wherein the pulsating field has a first amplitude-modulated waveform with an interference pattern, wherein the first spatial field and the second spatial field are superposed so that the interference pattern is a beat, and wherein an amplitude of the first amplitude-modulated waveform exceeds a predefined threshold.

7. The respiration promoting apparatus of claim 1, wherein the third spatial field and fourth spatial field are superposed and wherein the second interference pattern is a beat, and/or wherein an amplitude of the second amplitude-modulated waveform exceeds a predefined threshold.

8. The respiration promoting apparatus of claim 1, wherein each of the first field generator and the second field generator comprises a pair of electrode members, each pair of electrode members having two electrode patches, and wherein each of the electrode patches includes a body attachment structure and a multiplicity of electrodes that are mechanically attached to the body attachment structure.

9. The respiration promoting apparatus of claim 1, further comprising a biofeedback sensor configured to be positioned at the human such that it provides a feedback signal when a contraction of a diaphragm of the human occurs, wherein the controller is operably coupled to the biofeedback sensor and configured to automatically adjust the pulsating field until the feedback signal is received.

10. The respiration promoting apparatus of claim 9, wherein the controller is configured to automatically localize the phrenic nerve and/or the further phrenic nerve with respect to the field generators, and wherein the controller is further configured and arranged so as to repetitively output stimulation signals by the first and second field generators and the third and fourth field generators, respectively, when such a localization is made by the controller.

11. The respiration promoting apparatus of claim 9, comprising a second biofeedback sensor coupled to the controller, wherein the first biofeedback sensor is associated with the first spatial field and the second spatial field and the second biofeedback sensor is associated with the third spatial field and the fourth spatial field.

12. A method for promoting respiration by stimulating a phrenic nerve of a human, wherein the method comprises steps of:

generating by a first field generator a first spatial field having a first frequency and a first amplitude;

generating by a second field generator a second spatial field having a second frequency and a second amplitude;

controlling the first frequency and the second frequency so that the first spatial field and the second spatial field constructively and destructively interfere with each other, thereby forming a pulsating field for stimulating the phrenic nerve;

adjusting the pulsating field so that the phrenic nerve is positioned in the pulsating field; and generating a third spatial field by a third field generator and a fourth spatial field by a fourth field generator, so that the third spatial field and the fourth spatial field constructively and destructively interfere with each other to form a further pulsating field for stimulating a further phrenic nerve.

13. The method of claim 12, wherein the pulsating field has a first amplitude-modulated waveform with an interference pattern and the method further comprising superposing the first spatial field and the second spatial field so that the interference pattern is a beat.

14. The method of claim 13, wherein an amplitude of the first amplitude-modulated waveform exceeds a predefined threshold in a region, and wherein the method further includes controlling size, shaping and positioning of the region by adjusting the amplitude and by adjusting placement of the first field generator and the second field generator.

15. The method of claim 14, wherein controlling the size, shaping and positioning of the pulsating field is performed by adjusting relative amplitudes of the first spatial field and the second spatial field and by adjusting placement of the first field generator and the second field generator.

16. The method of claim 12, wherein at least one of the first field generator and the second field generator is not in phase.

17. The method of claim 12, wherein the first spatial field and the second spatial field are generated by a first electrode member pair and a second electrode member pair, respectively, wherein each of the first electrode member pair and the second electrode member pair comprises two electrode patches, and wherein each of the electrode patches includes a body attachment structure and a multiplicity of electrodes that are mechanically attached to the body attachment structure as to be in a predetermined orientation.

18. The method of claim 12, further comprising:

positioning a biofeedback sensor at the human, and providing a feedback signal using the biofeedback sensor when a contraction of a diaphragm of the human occurs;

adjusting the pulsating field until the feedback signal is received;

operably coupling a controller to the biofeedback sensor, and automatically adjusting the pulsating field by the controller until the feedback signal is received; and automatically localizing, by the controller, the phrenic nerve with respect to a given set of electrodes, and repetitively outputting stimulation signals by the first field generator and the second field generator upon receiving the feedback signal.

19. The method of claim 12, wherein a time of stimulation of the phrenic nerve differs from a time of stimulation of the further phrenic nerve.

20. The method of claim 12, further comprising:

positioning the first field generator on a neck of the human that is entirely on one side of a geometric plane; and positioning the second field generator on the neck of the human that is entirely on another side of the geometric plane, wherein the geometric plane intersects the neck of the human.

21. The method of claim 12, wherein an electric field is generated by an inductive source using time-varying magnetic fields.

22. The method of claim 12, wherein adjusting the pulsating field includes adjusting the first frequency and/or the second frequency to vary a frequency of the pulsating field.

23. The method of claim 12, wherein adjusting the pulsating field includes adjusting the first amplitude and/or the second amplitudes such that the phrenic nerve is positioned within the pulsating field.

* * * * *